United States Patent [19]
Smith et al.

[11] Patent Number: 5,467,779
[45] Date of Patent: Nov. 21, 1995

[54] MULTIPLANAR PROBE FOR ULTRASONIC IMAGING

[75] Inventors: Lowell S. Smith, Schenectady; Robert S. Lewandowski, Amsterdam, both of N.Y.

[73] Assignee: General Electric Company, Schenectady, N.Y.

[21] Appl. No.: 276,380

[22] Filed: Jul. 18, 1994

[51] Int. Cl.⁶ .................................................. A61B 8/12
[52] U.S. Cl. ............................. 128/660.1; 128/662.06
[58] Field of Search ............... 128/660.07–660.1, 128/662.03, 662.06; 73/633; 310/334; 29/25.35, 985

[56] References Cited

U.S. PATENT DOCUMENTS

| | | | |
|---|---|---|---|
| 4,211,948 | 7/1980 | Smith et al. | 310/322 |
| 4,217,684 | 8/1980 | Brisken et al. | 29/25.35 |
| 4,404,489 | 9/1983 | Larson, III et al. | 310/334 |
| 4,434,659 | 3/1984 | Furtz et al. | 73/620 |
| 4,543,960 | 10/1985 | Harui et al. | 128/660 |
| 4,747,192 | 5/1988 | Rokurota | 29/25.35 |
| 4,825,115 | 4/1989 | Kawabe et al. | 310/327 |
| 5,091,893 | 2/1992 | Smith et al. | 367/153 |
| 5,148,962 | 9/1992 | Jones et al. | 229/49.1 |
| 5,176,142 | 1/1993 | Mason | 128/662.06 |
| 5,181,514 | 1/1993 | Solomon et al. | 128/660.09 |
| 5,191,890 | 3/1993 | Hileman | 128/662.06 |
| 5,215,092 | 6/1993 | Wray | 128/660.09 |
| 5,226,422 | 7/1993 | McKeighen et al. | 128/662.06 |
| 5,237,743 | 8/1993 | Busacco et al. | 29/885 |
| 5,320,104 | 6/1994 | Fearnside et al. | 128/661.01 |
| 5,351,691 | 10/1994 | Brommersma | 128/662.06 |

OTHER PUBLICATIONS

"The Design of Efficient Broad–Band Piezoelectric Transducers". DeSilets et al., IEEE Trans. Sonics & Ultrasonics, vol. SU–25, No. 3, May 1978, pp. 115–125.

*Primary Examiner*—Francis Jaworski
*Attorney, Agent, or Firm*—Marvin Snyder

[57] ABSTRACT

A multiplanar ultrasonic probe incorporates a mechanically rotatable linear phased transducer array. The transducer array can be remotely maneuvered to change the scan plane. A ring gear affixed to the transducer array surrounds the transducer array and is concentric with the axis of rotation. The ring gear is engaged and rotated by an indexing mechanism in incremental angular steps in either the clockwise or counterclockwise direction. The indexing mechanism includes a ratchet mechanism displaceable along a line between first and second positions from a neutral position intermediate the first and second positions. The ratchet mechanism carries a pair of pawls, one of which engages the ring gear to cause clockwise rotation and the other of which engages the ring gear to cause counterclockwise rotation. The ratchet mechanism is displaced by actuators such as bimorphic devices, made of piezoelectric material, which bend in response to electrical pulsing.

11 Claims, 3 Drawing Sheets

MULTIPLANAR PROBE FOR ULTRASONIC IMAGING

FIELD OF THE INVENTION

This invention generally relates to probes used in anatomical ultrasonic imaging and, more particularly, to an ultrasonic probe useful in clinical examinations such as esophageal echocardiography.

BACKGROUND OF THE INVENTION

In conventional ultrasonic imaging, the ultrasonic probe is used extracorporeally. Therefore the operator has much flexibility in selecting the imaging plane. The operator can translate and rotate the probe as required to generate the most desirable image. However, acoustic access to some clinically interesting regions of the anatomy is limited by intervening structures. For example, in human adult echocardiology the ribs and lungs restrict acoustic access to a few standard views. Moreover, variations in body fat give rise to velocity inhomogeneities which degrade resolution in conventional ultrasonic imagers. For these reasons, esophageal echocardiography has undergone major advances in imaging the crucial central area of the heart. The left atrium, pulmonary veins, mitral valve area, subaortic area, and pulmonary arteries are all in close proximity from a posterior approach to probes placed in the esophagus. The internal probe thus avoids some of the hindrances to acoustic access; however, it also compromises the operator's ability to position the scan plane. Especially in congenital heart disease, where the anatomy is likely to be nonstandard, this limitation on scan plane selection can be a significant clinical problem.

A probe capable of generating several image planes from a known source position would be extremely useful in esophageal echocardiography. The ability to generate several image planes from a known source position would make it possible to reconstruct the data in three dimensions. Advances in three-dimensional medical imaging allow a series of two-dimensional images to be converted into three-dimensional renderings. One especially useful kind of presentation is the reconstruction of three-dimensional surfaces from the two-dimensional data. One approach to this problem as set forth in commonly-assigned U.S. Pat. No. 4,719,585, issued Jan. 12, 1988, is to use a "dividing cubes" algorithm which can be easily implemented by a digital signal processing accessory board for a computer workstation. Alternatively, software algorithms are well-developed for viewing objects from arbitrary directions and for selectively removing arbitrary volumes or surfaces to enable visualization of internal structures.

Esophageal echocardiography has been performed with a single linear phased array mounted near the probe tip generating a single, usually transverse, scan plane. The scanning limitations imposed by this arrangement have resulted in efforts to produce a biplane probe. These efforts led to fabrication of biplane esophageal probes with two right-angle oriented arrays at the tip (one transverse and one longitudinal), each with a separate wiring harness and consequently a large cable bundle that limits the probe's maneuverability. While producing two independent images at different locations, the increased probe size makes the scan plane selection even more difficult. There is an ongoing and continued need for continuous alteration of the scan plane of imaging, especially for clinical assessment of some forms of congenital heart disease.

Mechanical systems have been suggested involving angulation, or pivots of the tip of a phased array probe, for advancement or retraction of the probe as it moves along the esophagus, to localize the scan plane. These systems have not been clinically successful because the elasticity of the esophageal tissue tends to oppose the desired motion, leading to locally distorted anatomy and less displacement than expected. Such problems can be expected when the probe tip must move either axially or laterally along the surface of the tissue.

SUMMARY OF THE INVENTION

Briefly, in accordance with a preferred embodiment of the invention, a multiplanar ultrasonic probe designed to ameliorate the aforementioned difficulties contains a mechanically rotatable linear phased array. The probe is especially intended for use in clinical examinations like esophageal echocardiography, where the ultrasonic transducer array must be maneuvered in order to change the scan plane.

The transducer array is rotatably mounted inside a probe tip housing for rotation about an axis normal to the array front surface. In accordance with a preferred embodiment of the invention, a ring gear, which is concentric with the axis of rotation, surrounds and is affixed to, the transducer array. The ring gear is engaged by an indexing mechanism which rotates the ring gear, and hence the transducer array, in incremental angular steps. The array can be rotated in either the clockwise or counterclockwise direction. The indexing mechanism comprises a ratchet mechanism having a neutral position. When the ratchet mechanism is driven to displace in one direction by an actuating means, a first pawl mounted on the ratchet mechanism engages the teeth of the ring gear, causing the transducer array to rotate clockwise one angular increment. When the ratchet mechanism is driven to displace in the opposite direction by the actuating means, a second pawl mounted on the ratchet mechanism engages the teeth of the ring gear, causing the transducer array to rotate counterclockwise one angular increment. The actuating means can take the form of bimorphic devices made of piezoelectric material which bend in response to electrical pulsing. Alternatively, solenoids could be used.

An endoscope for employment in accordance with the invention includes an ultrasonic transducer array in its tip which can be rotated without use of cables or a drive shaft. The transducer array and rotation mechanisms are housed in the probe tip with only a few signal wires required to pass through the shaft of the probe for controlling the array rotation.

The probe design may optionally incorporate a sensor circuit to encode the angular position of the array during scanning. This allows both improved scan plane selection and true three-dimensional reconstruction of a localized volume of the heart. As a result, complex spatial relationships in the most clinically relevant areas of the heart can be better displayed.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

DETAILED DESCRIPTION OF THE PREFERRED EMBODIMENTS

Figure 1:
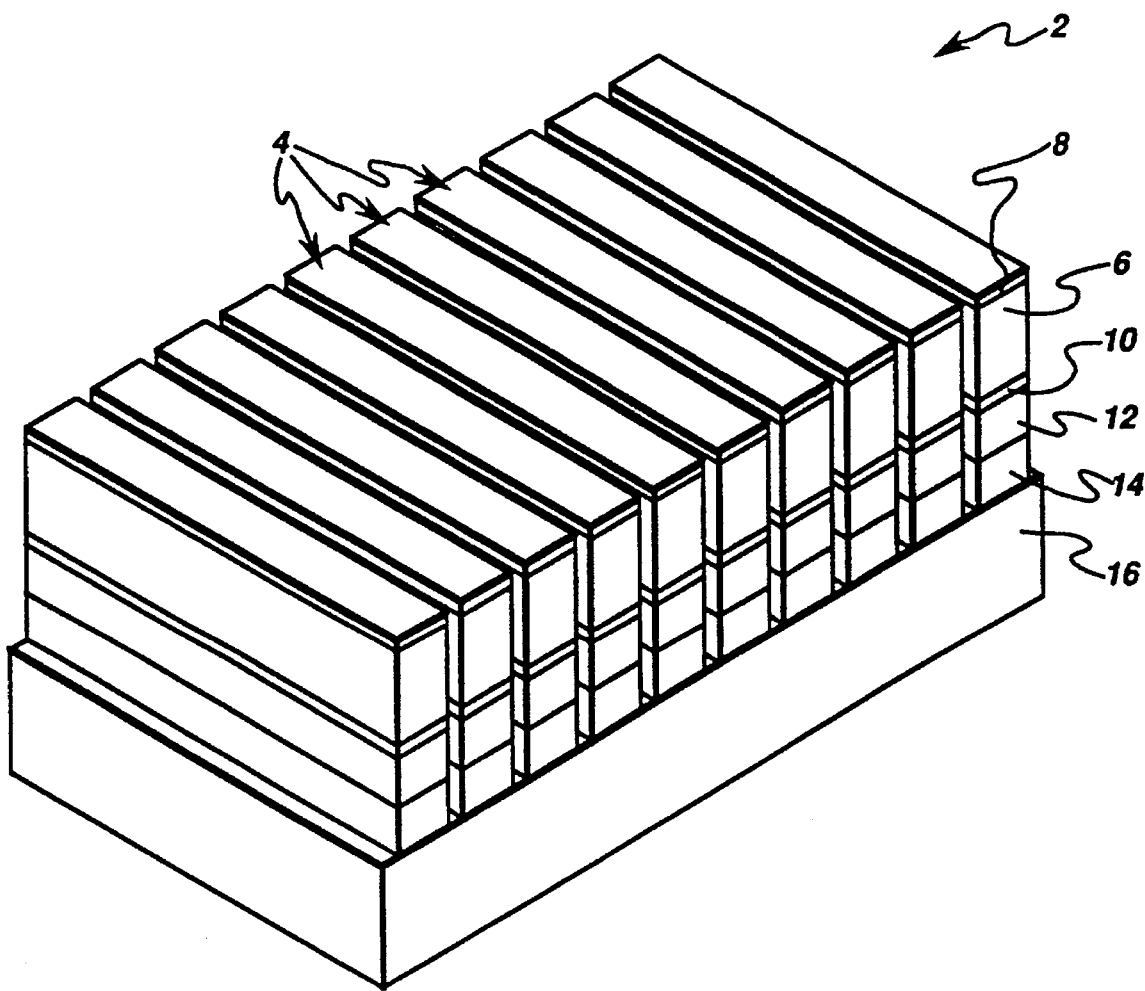
FIG. 1 is a perspective view of a conventional transducer array suitable for incorporation in the ultrasonic probe of the present invention.

FIG. 1 shows a conventional ultrasonic transducer array 2 suitable for incorporation in the probe of the present invention and comprised of a plurality of separately driven array elements 4. Each transducer element produces a burst of ultrasonic energy when energized by a pulsed waveform produced by a transmitter (not shown). The ultrasonic energy reflected back to transducer array 2 from an object under study is converted to an electrical signal by each receiving transducer element 4 and applied separately to a receiver (not shown).

Transducer array 2 is fabricated from a single plate of piezoelectric ceramic material (e.g., lead zirconate titanate) plated on opposite sides with a metallic coating (e.g. titanium or chromium, overlaid with copper) and bonded to one or more acoustic matching layers. Where two acoustic matching layers are used, the first acoustic matching layer is bonded to the second acoustic matching layer, which is itself bonded to a lens. The individual array elements 4 are formed by making parallel cuts (a process termed "dicing") through less than the full depth of the bonded composite, stopping short of the lens. The cuts are spaced at distances of one wavelength or less at the emission frequency. As seen in FIG. 1, each array element 4 comprises a narrow piezoelectric ceramic array element 6, which has metallic coatings on opposite faces thereof to serve respectively as a signal electrode 8 and a ground electrode 10, and first and second impedance matching layers 12 and 14. The design and fabrication of individual transducer elements with desirable acoustic properties, e.g., high sensitivity, wide bandwidth, short impulse response, and wide field of view, is a well-known art. Techniques for constructing piezoelectric transducer arrays can be found in numerous patents and publications, including U.S. Pat. Nos. 4,825,115, 4,747,192, 4,217,684 and 4,211,948 and an article by DeSilets et al. appearing in IEEE Trans. Son. Ultrason., SU-25, 115 (1978).

Array elements 4 are acoustically coupled to a lens 16 which may be a compound lens having a cylindrical surface (not shown in FIG. 1) for focusing the ultrasonic energy emitted by the transducer array along a plane parallel to the array elements, as described in U.S. Pat. No. 5,181,514. Suitable means may be provided between lens 16 and an opposing portion of a probe tip housing 18 (see FIG. 2) to ensure acoustic coupling between the lens and the housing in conventional manner. Likewise a mass of suitable acoustical damping material can be positioned at the back surface of the transducer array.

Figure 2:
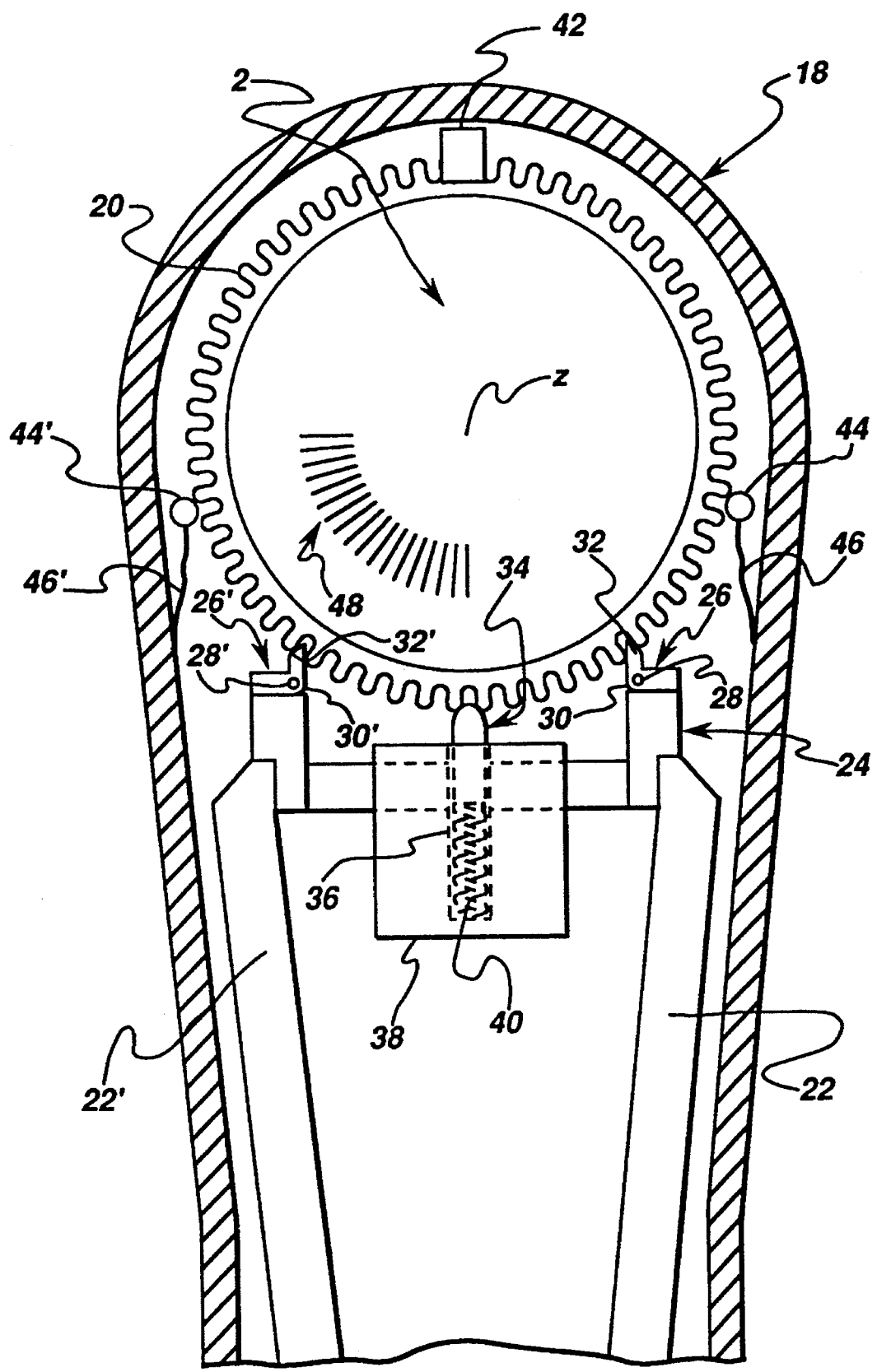
FIG. 2 is a partially sectional front view showing an arrangement for actuating rotation of the transducer array in accordance with a preferred embodiment of the invention.

As shown in FIG. 2, the probe tip housing provides the axis for rotation of a shaft (not shown) supporting transducer array 2. The transducer array itself is either circular through apodization or is mounted on a circular platform. A circular lip or groove (not shown) in the housing holds the array pallet in place. Alternatively, any other suitable bearing can be used in conjunction with appropriate seals, as is conventional in the art. At the other side, the shaft fits into a molded recessed hole (not shown) to establish a rotation axis Z extending through the center of the array.

In accordance with a preferred embodiment of the invention, a ring gear 20 is fixedly mounted on the periphery of transducer array 2. Ring gear 20 has a plurality of radially outwardly extending teeth circumferentially distributed at equal angular intervals along its periphery. The regularly spaced teeth enable array 2 to be rotated in uniform incremental angular steps by actuator 22 or 22' via a ratchet mechanism 24, which has one end mounted on the end of actuator 22 and the other end mounted on the end of actuator 22'.

Ratchet mechanism 24 includes a pair of pawls 26, 26' mounted on respective pivot pins 28, 28'. Each pawl has a rounded corner 30, 30' the surface of which forms a 90° arc centered at the axis of the corresponding pivot pin 28, 28'. Rounded corners 30, 30' enable pawls 26, 26' to pivot 90°. Each pawl 26, 26' further includes a tooth 32, 32', respectively, which meshes with the teeth of ring gear 20. Each gear tooth produces an index point for each step of rotation of the transducer array. Rotation of the pivots facilitates disengagement of the pawl tooth and the ring gear teeth, as described in detail hereinbelow.

Actuators 22 and 22' are controlled by an actuator controller (not shown). Actuators 22 and 22' are preferably bimorphic devices constructed of piezoelectric material which bends in response to electrical pulses from the actuator controller. Thus actuator 22 actuates clockwise rotation of array 2 by bending to cause leftward displacement of ratchet mechanism 24. As pawl 26 displaces leftward into engagement with the ring gear teeth, it causes clockwise rotation of transducer array 2. This rotation of transducer array 2 causes a detent 34 to disengage from its present tooth of ring gear 20 and then engage the next tooth of ring gear 20. As the ratchet mechanism 24 returns to its neutral position, pawl 26 pivots counterclockwise to cause no counterclockwise rotation of the transducer array 2. Similarly, actuator 22' actuates counterclockwise rotation of array 2 by bending to cause rightward displacement of ratchet mechanism 24. As pawl 26' displaces rightward into engagement with the ring gear teeth, it causes counterclockwise rotation of transducer array 2. This rotation of transducer array 2 causes detent 34 to disengage from its present tooth of ring gear 20 and then engage the next tooth of ring gear 20. As the ratchet mechanism 24 returns to its neutral position, pawl 26' pivots clockwise to cause no clockwise rotation of the transducer array 2.

Depending on the type of bimorphic devices being used, the actuators may work together instead of independently. By using bimorphic devices that actuate in one or the other direction depending on polarity of the signal, clockwise rotation can be achieved by pulsing one actuator to move to the left at the same time that the other actuator is pulsed to move to the left. For counterclockwise rotation, polarity of the signal to both actuators is reversed, causing them to both move to the right. In this latter preferred embodiment, the actuators are connected to the ratchet mechanism in a manner that allows them to push and pull on the ratchet mechanism.

When the transducer array is not being rotated, it is held stationary at a predetermined angular position by detent 34 which is slidably arranged inside a circular cylindrical bore 36 formed in a solid block 38. Block 38 is rigidly supported by probe tip housing 18. A compression spring 40 seated inside bore 36 urges the detent toward a position whereat the tip of the detent engages the teeth on ring gear 20. If no torque is being applied to the ring gear by either of pawls 26 and 26', e.g., during the intervals between indexing steps, then detent 34 holds transducer array 2 stationary.

An array stop 42 is securely inserted in a recess formed on the periphery of ring gear 20. Array stop 42 protrudes radially outward beyond the radial extent of the ring gear teeth. Upon sufficient angular displacement of transducer array 2 in a clockwise direction about axis Z, array stop 42 will abut a stop pin 44. Stop pin 44 is securely mounted on probe tip housing 18 and is electrically coupled to the actuator controller via a conductor 46. When array stop 42 engages stop pin 44, a feedback signal is sent to the actuator controller. This can be accomplished, for example, by providing a switch (not shown) which is closed when the array stop impinges on the stop pin. In response to such feedback signal, the actuator controller ceases to index the transducer array in the clockwise direction. Similarly, upon sufficient angular displacement of transducer array 2 in a counter-clockwise direction about axis Z, array stop 42 will abut a stop pin 44', which is securely mounted on probe tip housing 18 and is electrically coupled to the actuator controller via a conductor 46'. When array stop 42 engages stop pin 44', a feedback signal is sent to the actuator controller. In response to that feedback signal, the actuator controller ceases to index the transducer array in the counter-clockwise direction. Thus the stop pins limit angular displacement of transducer array to a predetermined range.

Optionally, an optical transducer can be used to encode the angular position of transducer array 2. For example, a surface of the transducer array may be provided with a plurality of reflective radial marks 48 spaced at equal angular intervals of 360°/N where N is the number of teeth on the periphery of ring gear 20. Alternatively, other conventional marking schemes can be used. An LED (light-emitting diode) and a photodetector (not shown) may be mounted inside the probe tip housing at positions such that light transmitted by the LED impinges on the radial marks and is reflected thereby toward the photodetector. Thus the photodetector produces an output pulse each time the transducer array is indexed. The minimum number of radial marks needed to track angular position of the array is ($\theta$/360°)N, where $\theta$ is the range of angular displacement allowed by the stop pins. Alternatively, any other suitable conventional position encoder can be used.

Electrical connections to the rotatable acoustic array are a crucial aspect of a multiplanar probe. By initially limiting the scan plan rotation, the multiplanar positioning can be achieved with minimal stress on the electrical connections. In order to attach the coaxial leads to the individual transducer elements, some intermediate structure is used. In the conventional design, a rigid fiber-epoxy printed circuit board is placed behind the ceramic with photolithographed conductive runs connecting pads for the wire bonds and solder pads for the cable connections. The pressure produced by the wire bonder and the solder pad size become limiting factors for these miniature probes.

Figure 3:
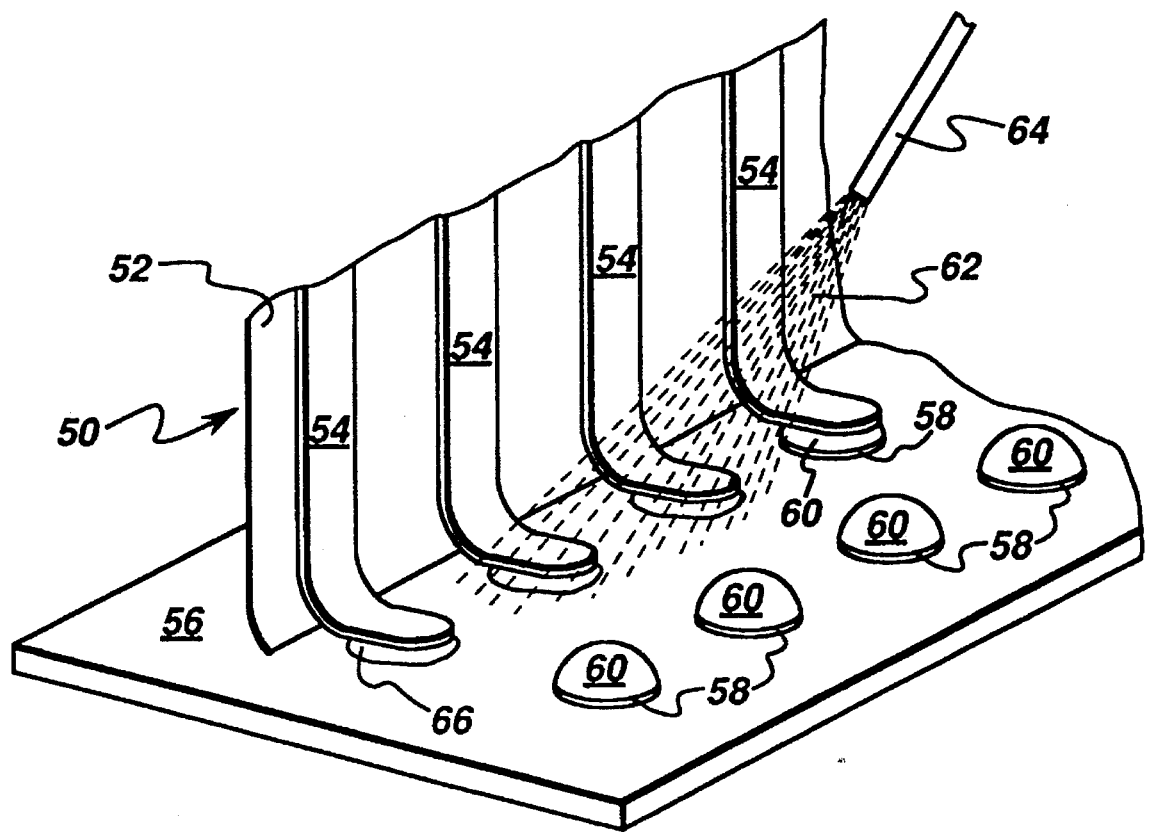
FIG. 3 is a schematic illustration of one technique for forming solder joints between a flexible printed circuit board and a substrate of a rotatable transducer array in accordance with the present invention.

Two connection methods provide ways to avoid these problems and create smaller high-frequency transducer arrays. The simpler approach uses conventional flexible printed circuit board technology with high-resolution lithography (25 µm lines and spaces). The lines of the flexible circuit board are directly connected to the piezoelectric ceramic, which is subsequently diced. A technique for constructing this direct connection is disclosed in commonly assigned Jones et al. U.S. Pat. No. 5,148,962, issued Sep. 22, 1992 and incorporated herein by reference. The aforesaid technique of U.S. Pat. No. 5,148,962 is partially depicted in FIG. 3 herein. The flexible printed circuit board (PCB) 50 is comprised of a polyimide sheet 52, which is coated with a conductive copper laminate. After the conductor pattern on the flexible PCB has been produced by a conventional photolithographic technique, an edge of polyimide sheet 52 perpendicular to the direction of the conductor runs or leads thereon is etched away by a conventional etching technique until finger leads 54 remain which extend beyond the edge of polyimide sheet 52. The finger leads are then tinned by a conventional metal coating technique.

The substrate 56, which constitutes the undiced transducer array, is metallized by conventional metal coating techniques such as sputtering or electroplating to produce the metal layer from which the output electrodes are to be fabricated. Additional metallic pads 58 with a thickness of 4–7 µm and a diameter of approximately 75 µm are placed on top of the metallized substrate by a conventional electroplating technique. Then a suitable solder is electroplated to the tops of metallic pads 58 to create solder pads 60 each having a thickness of 10–20 µm. The number of solder pads created in accordance with the foregoing technique equals the number of finger leads. The solder pads are situated such that each pad aligns with a corresponding finger lead when the flexible PCB is brought into physical contact with substrate 56 which, for heat removal purposes, is typically supported on an alumina substrate (not shown) during the process of bonding the finger leads to the solder pads.

When finger leads 54 are in physical contact with solder pads 60, if the desired flexure and electrical contact have been established, a laser beam 62, as from an optical fiber 64, impinges on a plurality of leads 54, causing solder pads 60 to begin to melt and reflow. This causes finger leads 54 to be pulled down and become permanently bonded to metallic pads 58. Laser beam 62 traverses the entire lengths of finger leads 54 until a solder joint 66 is formed between each lead 54 and a respective pad 58. In this way the flexible PCB 50 is rigidly connected to the substrate.

The other approach for connecting a flexible PCB to a rotatable transducer array is a variation of a known high-density interconnect process originally developed for integrated circuit packaging and disclosed in commonly assigned Smith et al. U.S. Pat. No. 5,091,893 issued Feb. 25, 1992 and incorporated herein by reference. Using this technique, a flexible PCB can be fabricated with one end directly connected to a transducer array. To accomplish this, the transducer array is placed in a well formed in a frame, with the metallized piezoceramic exposed. An insulating polyimide film is laminated to the surface of the metallized piezoceramic and the surrounding frame, creating a relatively flat surface. A computer-controlled laser then ablates holes in the polyimide layer down to the metal electrode atop the ceramic. A metal layer is applied over the film and follows the hole contours, thereby making electrical contact with the metal electrodes on the ceramic. Conventional photolithographic techniques (25 µm lines and spaces are typical) are used to pattern the metal, thus creating lines from each transducer element to a fanout pattern. The process can be repeated to produce multilayered structures. Excess polyimide can be removed to provide a good acoustic contact of the backing to the ceramic element.

Using either of the above-described methods, the resultant flexible PCB can have signal runs which fan out so that the miniature coaxial cables can be attached directly. Since the circuit board is flexible, the wiring assembly can be folded to occupy a very small cross section while retaining considerable freedom for motion. This feature can be exploited for multiplanar imaging.

The foregoing preferred embodiments have been disclosed for the purpose of illustration. Variations and modifications which do not depart from the broad concept of the invention will be readily apparent to those skilled in the art; for example, other techniques for achieving transducer array rotation can be utilized. In accordance with one alternative, the transducer pallet is mounted on a turntable with a restoring spring and an externally manipulated wire rotates the assembly. In accordance with a second alternative, a miniature stepper motor with timed pulses through current loops can be used to apply either a torque or a holding force. All such variations and modifications are intended to be encompassed by the claims set forth hereinafter.

What is claimed is:

1. A multiplanar probe comprising, an array of ultrasonic transducers, each of said transducers including an output electrode, said probe further comprising means for rotating the transducer array about an axis of rotation, the rotating means comprising a ring gear affixed to said transducer array, said ring gear having a plurality of teeth distributed at equal angular intervals on its periphery, and indexing means for driving said ring gear to rotate in angular steps, said indexing means comprising a ratchet mechanism having first and second pawls, and means for displacing said ratchet mechanism between first and second positions, said first pawl being engaged with said teeth of said ring gear and said second pawl being disengaged from said teeth of said ring gear when said ratchet mechanism is in said first position, and said first pawl being disengaged from said teeth of said ring gear and said second pawl being engaged with said teeth of said ring gear when said ratchet mechanism is in said second position, a flexible printed circuit board having terminals thereon, and means coupling said terminals to the output electrodes of the transducer array.

2. The multiplanar probe as defined in claim 1, wherein said means for displacing said ratchet mechanism comprises first and second bimorphic devices, each of said bimorphic devices being comprised of piezoelectric material which bends in response to application of an electrical pulse thereto, said first and second bimorphic devices being arranged to displace said ratchet mechanism between said first and second positions in response to electrical pulses applied thereto.

3. The multiplanar probe as defined in claim 2, further comprising detent means for preventing rotation of said ring gear during intervals between successive indexing steps, and spring means for urging said detent means into engagement with said teeth of said ring gear.

4. A multiplanar probe comprising, an array of ultrasonic transducers, each of said transducers including an output electrode, said probe further comprising:

means for rotating the transducer array about an axis of rotation, the rotating means comprising a ring gear affixed to said transducer array, said ring gear having a plurality of teeth distributed at equal angular intervals on its periphery, and indexing means for driving said ring gear to rotate in angular steps;

a flexible printed circuit board having terminals thereon;

means coupling said terminals to the output electrodes of the transducer array;

a housing, said probe being situated within said housing;

array stop means mounted on said periphery of said ring gear and extending radially outward beyond the radial extent of said teeth;

first and second stop pins mounted on said housing, said first stop pin being arranged to engage said array stop means when said transducer array is at a first angular position and said second stop pin being arranged to engage said array stop means when said transducer array is at a second angular position; and feedback means for signaling impingement of said array stop means on said first or second stop pin to prevent actuation of said indexing means to rotate said ring gear beyond said first or second stop pin, respectively.

5. A multiplanar probe comprising, an array of ultrasonic transducers, each of said transducers including an output electrode, said probe further comprising:

means for rotating the transducer array about an axis of rotation, the rotating means comprising a ring gear affixed to said transducer array, said ring gear having a plurality of teeth distributed at equal angular intervals on its periphery, and indexing means for driving said ring gear to rotate in angular steps;

a flexible printed circuit board having terminals thereon;

means coupling said terminals to the output electrodes of the transducer array;

a housing, said probe being situated within said housing;

array stop means mounted on said periphery of said ring gear and extending radially outward beyond the radial extent of said teeth;

first and second stop pins mounted on said housing, said first stop pin being arranged to engage said array stop means when said transducer array is at a first angular position and said second stop pin being arranged to engage said array stop means when said transducer array is at a second angular position;

feedback means for signaling impingement of said array stop means on said first or second stop pin to prevent actuation of said indexing means to rotate said ring gear beyond said first or second stop pint respectively; and position encoding means for detecting the angular position of said transducer array.

6. A multiplanar probe comprising, an array of ultrasonic transducers, each of said transducers including an output electrode, said probe further comprising a ring gear affixed to said transducer array for rotating the transducer array about an axis of rotation, said ring gear being connected to said array and having a plurality of teeth distributed at equal angular intervals on its periphery, and indexing means for driving said ring gear to rotate in angular steps, said indexing means comprising a ratchet mechanism having first and second pawls, and means for displacing said ratchet mechanism between first and second positions, said first pawl being engaged with said teeth of said ring gear and said second pawl being disengaged from said teeth of said ring gear when said ratchet mechanism is in said first position, and said first pawl being disengaged from said teeth of said ring gear and said second pawl being engaged with said teeth of said ring gear when said ratchet mechanism is in said second position.

7. The multiplanar probe as defined in claim 6, wherein said means for displacing said ratchet mechanism comprises first and second bimorphic devices, each of said bimorphic devices being comprised of piezoelectric material which bends in response to application of an electrical pulse thereto, said first and second bimorphic devices being arranged to displace said ratchet mechanism between said first and second positions in response to electrical pulses applied thereto.

8. The multiplanar probe as defined in claim 7, further comprising detent means for preventing rotation of said ring gear during intervals between successive indexing steps, and spring means for urging said detent means into engagement with said teeth of said ring gear.

9. The multiplanar probe as defined in claim 6, further comprising position encoding means for detecting the angular position of said transducer array.

10. The multiplanar probe as defined in claim 6, wherein said first and second pawls are pivotably mounted on said ratchet mechanism, each of said pawls being rotatable over a predetermined angular range of less than 360°.

11. A multiplanar probe comprising, an array of ultrasonic transducers, each of said transducers including an output electrode, said probe further comprising:

a ring gear affixed to said transducer array for rotating the transducer array about an axis of rotation, said ring gear being connected to said array and having a plurality of teeth distributed at equal angular intervals on its periphery;

indexing means for driving said ring gear to rotate in angular steps;

a housing, said probe being situated within said housing;

array stop means mounted on said periphery of said ring gear and extending radially outward beyond the radial extent of said teeth;

first and second stop pins mounted on said housing, said first stop pin being arranged to engage said array stop means when said transducer array is at a first angular position and said second stop pin being arranged to engage said array stop means when said transducer array is at a second angular position; and feedback means for signaling impingement of said array stop means on said first or second stop pin to prevent actuation of said indexing means to rotate said ring gear beyond said first or second stop pin, respectively.

* * * * *